United States Patent
Cholette

(10) Patent No.: US 8,255,051 B2
(45) Date of Patent: Aug. 28, 2012

(54) SKIN RESPONSE MONITORING FOR NEURAL AND CARDIAC THERAPIES

(75) Inventor: Martin Cholette, Acton, CA (US)

(73) Assignee: Pacesetter, Inc., Sylmar, CA (US)

( * ) Notice: Subject to any disclaimer, the term of this patent is extended or adjusted under 35 U.S.C. 154(b) by 287 days.

(21) Appl. No.: 12/783,427

(22) Filed: May 19, 2010

(65) Prior Publication Data

US 2011/0288607 A1 Nov. 24, 2011

(51) Int. Cl.
*A61N 1/36* (2006.01)

(52) U.S. Cl. .......................... 607/18; 600/310

(58) Field of Classification Search ............... 607/18; 128/903; 600/310, 407, 587
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,940,052 A | 7/1990 | Mann et al. | |
| 4,944,298 A | 7/1990 | Sholder | |
| 5,466,254 A | 11/1995 | Helland | |
| 5,476,483 A | 12/1995 | Bornzin et al. | |
| 5,601,611 A * | 2/1997 | Fayram et al. | 607/6 |
| 5,911,689 A * | 6/1999 | Smith et al. | 600/310 |
| 6,298,253 B1 * | 10/2001 | Buschmann | 600/338 |
| 6,314,323 B1 | 11/2001 | Ekwall | |
| 7,122,012 B2 * | 10/2006 | Bouton et al. | 600/587 |
| 7,512,431 B2 * | 3/2009 | Roberts | 600/332 |
| 7,582,061 B2 | 9/2009 | Li et al. | |
| 7,647,095 B2 | 1/2010 | Bhunia | |
| 7,738,935 B1 * | 6/2010 | Turcott | 600/336 |
| 2007/0239053 A1 | 10/2007 | Bhunia | |
| 2007/0255148 A1 | 11/2007 | Bhunia | |
| 2009/0131999 A1 | 5/2009 | Li et al. | |

FOREIGN PATENT DOCUMENTS

| | | |
|---|---|---|
| WO | 2007117843 A1 | 10/2007 |
| WO | 2007127675 A1 | 11/2007 |

OTHER PUBLICATIONS

Brenner, Richard P., "Electroencephalography in Syncope," J Clin Neurophysiol. 1997;14(3):197-209.
Deltombe, Thierry MD et al., "The Influence of Skin Temperature on Latency and Amplitude of the Sympathetic Skin Response in Normal Subjects," Muscle Nerve. 1998;21(1):34-39.
Ratz, Paul H. et al., "Effects of acute myocardial infarction on the circulation of the conscious rat," J Auton Nerv Syst. 1986;16(4):249-259.

* cited by examiner

*Primary Examiner* — Brian T Gedeon

(57) ABSTRACT

An exemplary method includes emitting radiation subcutaneously; sensing at least some of the emitted radiation as reflected cutaneously; detecting an abnormal physiologic condition; and, based at least in part on the sensing, adjusting a stimulation therapy to treat the detected abnormal condition. In such a method, the abnormal condition may be an abnormal cardiac condition, an abnormal neural condition or other condition. Various other methods, devices, systems, etc., are also disclosed.

21 Claims, 10 Drawing Sheets

SKIN RESPONSE MONITORING FOR NEURAL AND CARDIAC THERAPIES

TECHNICAL FIELD

Subject matter presented herein relates generally to skin response monitoring for therapy systems (e.g., cardiac therapies, neural therapies, etc.).

BACKGROUND

Plethysmography has been used to measure waveforms of the arterial vasculature. For example, U.S. Pat. No. 6,491,639 to Turcott, which is incorporated by reference herein, describes an implantable device with plethysmography circuitry for acquisition of such waveforms. Specifically, a waveform can provide arterial pulse amplitude. Depending on placement of the plethysmography sensor, a few tens to a few hundreds of milliseconds after a QRS complex, a waveform voltage may reach a minimum and start to increase as blood volume increases in the sensed arterioles. Where the sensor is positioned subcutaneously in a pectoral pocket directed away from the surface of the body, a wide-band voltage waveform reaches a peak after about 100 msec. In this example, the excursion from minimum to maximum represents the arterial pulse amplitude. During diastole the recoil of the elastic arterial vessels continues to force blood through the capillaries, so that blood flows through the capillary bed throughout the entire cardiac cycle. The decrease in blood volume on the arterial side during diastole results in the decrease in the plethysmography waveform during this period. For a narrow-band voltage waveform, the maximum may occur within about 100 msec of a QRS complex and the minimum thereafter within about 200 msec of the QRS complex. Again, in the foregoing example, a delay exists between cardiac action and the sensed voltage based in part on distance between the sensor and the heart.

As described herein, various exemplary techniques provide skin response information, optionally using a plethysmographic sensor. Such information may be applied to one or more types of therapy (e.g., cardiac therapies, neural therapies, etc.).

SUMMARY

An exemplary method includes emitting radiation subcutaneously; sensing at least some of the emitted radiation as reflected cutaneously; detecting an abnormal physiologic condition; and, based at least in part on the sensing, adjusting a stimulation therapy to treat the detected abnormal physiologic condition. In such a method, the abnormal physiologic condition may be an abnormal cardiac condition, an abnormal neural condition or other physiologic condition. Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
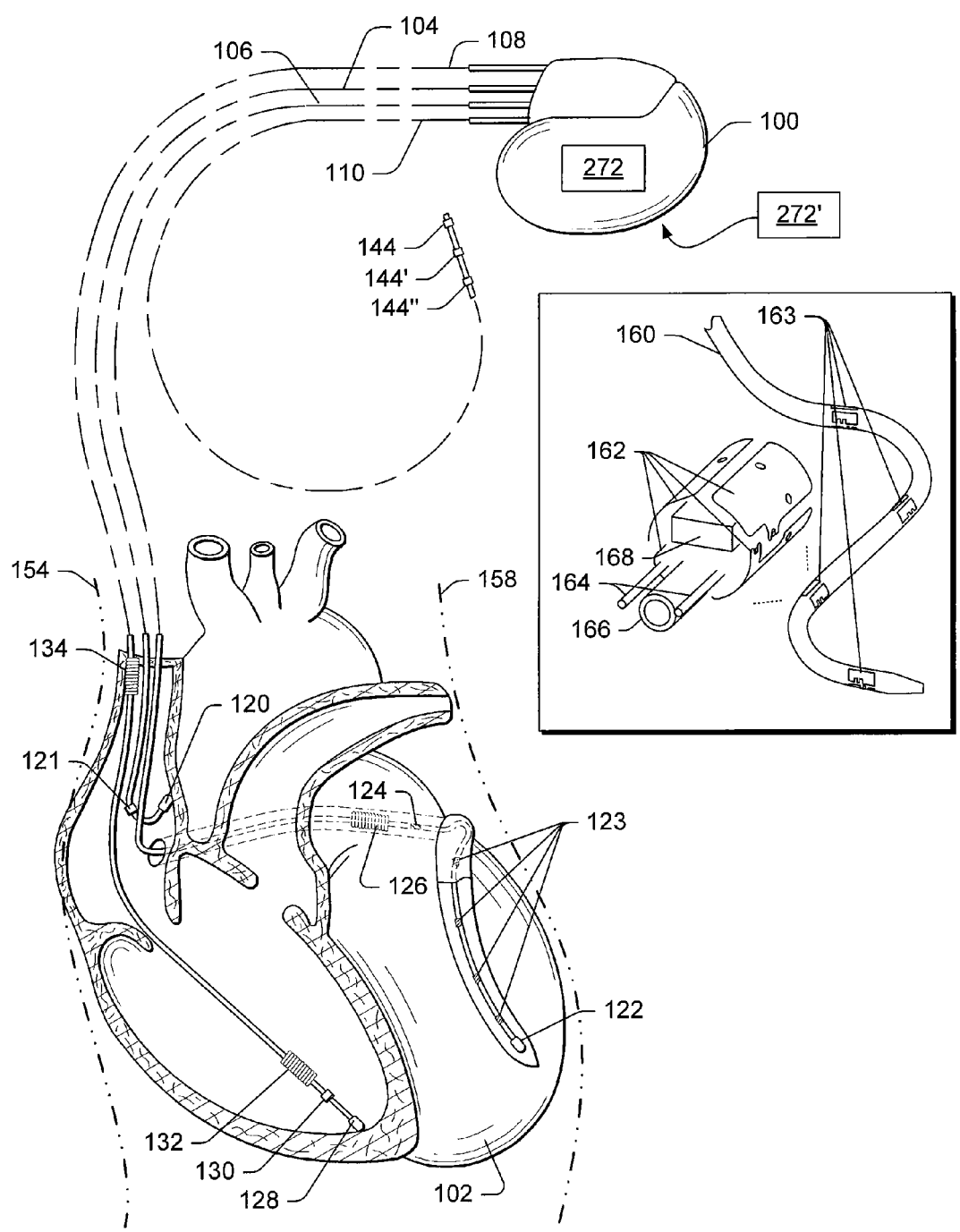
FIG. 1 is a simplified diagram illustrating an exemplary implantable stimulation device in electrical communication with at least three leads implanted into a patient's heart and at least one other lead for sensing and/or delivering stimulation and/or shock therapy. Approximate locations of the right and left phrenic nerves are also shown. Other devices with more or fewer leads may also be suitable for implementation of various exemplary techniques described herein.

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are typically used to reference like parts or elements throughout.

Various exemplary techniques described herein provide skin response information to aid diagnosis of one or more conditions or delivery of one or more types of therapies. Skin tends to be vascularized and highly innervated. Skin can respond quickly to changes in sympathetic tone. For example, a physical or psychological event can prompt an immediate sympathetic response that causes cutaneous vasoconstriction, which may turn a patient "white as a ghost." Such vasoconstriction can make a patient's skin feel "clammy."

Clammy skin (moist, cool, and usually pale) can be a sympathetic response to stress, for example, where stress causes release of hormones such as epinephrine and norepinephrine (noting that other hormones may be involved). Such hormones can cause cutaneous vasoconstriction and secretion of cold sweat from eccrine glands. Clammy skin may be a consequence of shock, acute hypoglycemia, anxiety reactions, arrhythmias, heat exhaustion, etc.

Clammy skin may also occur as a vasovagal reaction to severe pain associated with nausea, anorexia, epigastric distress, hyperpnea, tachypnea, weakness, confusion, tachycardia, and pupillary dilation or a combination of thereof (e.g., consider hormones such as vasopressin). In some instances, marked bradycardia and syncope may follow. As to psychological events, fainting upon sight of blood (e.g., venipuncture vasodepressor syncope) can occur within seconds.

An article by Brenner ("Electroencephalography in Syncope," Journal of Clinical Neurophysiology: May 1997, Vol. 14:3, pp. 197-209) provides a review electroencephalographic (EEG) findings for syncope. Brenner notes four major categories of syncope: neurally mediated (neurocardiogenic), neurologic, decreased cardiac output, and orthostatic hypotension. Brenner further notes that where EEGs are performed to evaluate of an episode of loss of consciousness, simultaneous ECG should be used. As described herein, skin response information may optionally be a surrogate for at least some of the type of information provided by an EEG.

While vasoconstriction and vasodilation may alter skin temperature, skin also responds to temperature. For example, initial exposure to a cold temperature can cause vasoconstriction as the body attempts to preserve heat. Further, the response of skin to sympathetic activity can vary with respect to temperature (see, e.g., Deltombe et al., "The influence of skin temperature on latency and amplitude of the sympathetic skin response in normal subjects," Muscle & Nerve, Vol. 21:1, pp. 34-39, 1998). Accordingly, various exemplary techniques optionally include temperature sensing.

In various examples that include a subcutaneous optical sensor oriented toward a skin surface, ambient radiation correction circuitry may be implemented to account for changes in ambient radiation. For example, where a patient has a subcutaneous optical sensor placed in a pectoral pocket and removes his shirt (e.g., at a beach or pool), circuitry may account for increased ambient radiation by establishing a baseline or by optionally by suspending sensing until ambient radiation drops below a particular level. One or more types of filtering may be optionally implemented to increase signal-to-noise for sensing skin responses (e.g., due to vasoconstriction, vasodilation or other causes).

Figure 2:
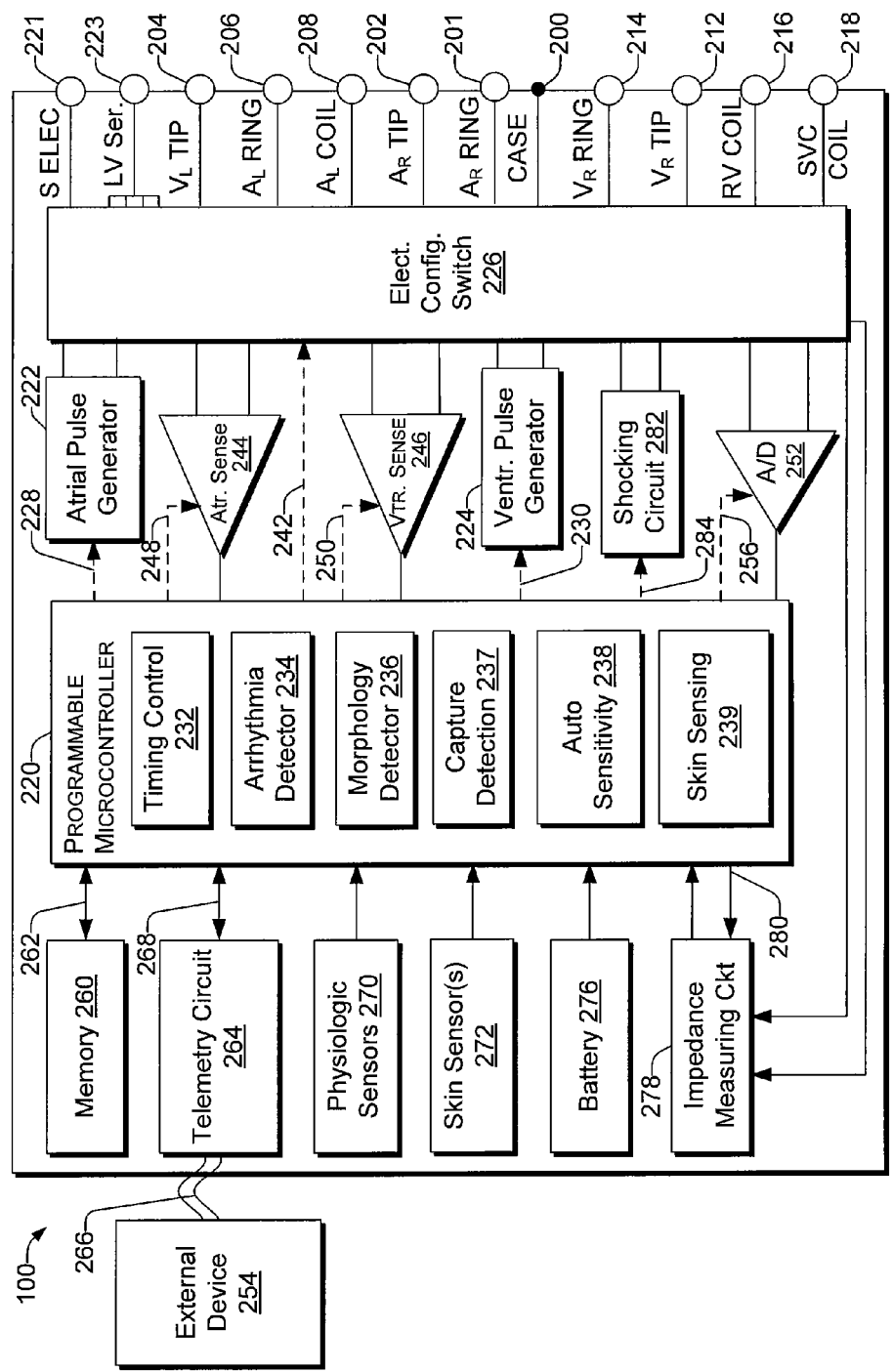
FIG. 2 is a functional block diagram of an exemplary implantable stimulation device illustrating basic elements that are configured to provide tissue stimulation. The implantable stimulation device is further configured to sense information and administer therapy responsive to such information.

Various techniques described below may be implemented in connection with a device configured or configurable for cardiac therapy, nerve therapy or one or more other types of therapy. With reference to FIGS. 1 and 2, an exemplary stimulation device is described, configured or configurable for delivery of one or more types of stimulation therapy.

FIG. 1 shows an exemplary stimulation device 100 in electrical communication with a patient's heart 102 by way of three leads (a right atrial lead 104, a left ventricular lead 106 and a right ventricular lead 108), suitable for delivering multi-chamber stimulation and shock therapy. The leads 104, 106, 108 are optionally configurable for delivery of stimulation pulses suitable for stimulation of nerves or other tissue. In addition, in the example of FIG. 1, the device 100 includes a fourth lead 110 having multiple electrodes 144, 144', 144" suitable for stimulation of tissue and/or sensing of physiologic signals. This lead may be positioned in and/or near a patient's heart and/or remote from the heart.

FIG. 1 also shows approximate locations of the right and left phrenic nerves 154, 158. The phrenic nerve is made up mostly of motor nerve fibres for producing contractions of the diaphragm. In addition, it provides sensory innervation for various components of the mediastinum and pleura, as well as the upper abdomen (e.g., liver and gall bladder). The right phrenic nerve 154 passes over the brachiocephalic artery, posterior to the subclavian vein, and then crosses the root of the right lung anteriorly and then leaves the thorax by passing through the vena cava hiatus opening in the diaphragm at the level of T8. More specifically, with respect to the heart, the right phrenic nerve 154 passes over the right atrium while the left phrenic nerve 158 passes over the pericardium of the left ventricle and pierces the diaphragm separately. While certain therapies may call for phrenic nerve stimulation (e.g., for treatment of sleep apnea or hypoxia), in general, cardiac pacing therapies avoid phrenic nerve stimulation through judicious lead and electrode placement, selection of electrode configurations, adjustment of pacing parameters, etc.

Referring again to the various leads of the device 100, the right atrial lead 104, as the name implies, is positioned in and/or passes through a patient's right atrium. The right atrial lead 104 is configured to sense atrial cardiac signals and/or to provide right atrial chamber stimulation therapy. As described further below, the right atrial lead 104 may be used by the device 100 to acquire far-field ventricular signal data. As shown in FIG. 1, the right atrial lead 104 includes an atrial tip electrode 120, which typically is implanted in the patient's right atrial appendage, and an atrial ring electrode 121. The right atrial lead 104 may have electrodes other than the tip 120 and ring 121 electrodes. Further, the right atrial lead 104 may include electrodes suitable for stimulation and/or sensing located on a branch.

To sense atrial cardiac signals, ventricular cardiac signals and/or to provide chamber pacing therapy, particularly on the left side of a patient's heart, the stimulation device 100 is coupled to the left ventricular lead 106, which in FIG. 1 is also referred to as a coronary sinus lead as it is designed for placement in the coronary sinus and/or tributary veins of the coronary sinus. As shown in FIG. 1, the coronary sinus lead 106 is configured to position at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method may select one or more electrodes (e.g., from electrodes 123 of the lead 106) and determine characteristics associated with rhythm, conduction and/or timing in the heart to aid in ventricular pacing therapy and/or assessment of cardiac condition.

In the example of FIG. 1, as connected to the device 100, the coronary sinus lead 106 is configured for acquisition of ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a particular coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava.

Accordingly, the right ventricular lead 108, as connected to the device 100, is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

FIG. 1 also shows a lead 160 as including several electrode arrays 163. In the example of FIG. 1, each electrode array 163 of the lead 160 includes a series of electrodes 162 with an associated circuit 168. Conductors 164 provide an electrical supply and return for the circuit 168. The circuit 168 includes control logic sufficient to electrically connect the conductors 164 to one or more of the electrodes of the series 162. In the example of FIG. 1, the lead 160 includes a lumen 166 suitable for receipt of a guidewire to facilitate placement of the lead 160. As described herein, any of the leads 104, 106, 108 or 110 may include one or more electrode array, optionally configured as the electrode array 163 of the lead 160.

As described in more detail below, the device 100 includes one or more sensors 272. While the example of FIG. 1 shows the one or more sensors 272 as being located on an outward facing side of the device 100, various exemplary arrangements may include one or more sensors located on an inward facing side of the device 100. For example, many ICDs are implanted in a pectoral pocket with one side facing inward toward muscle (pectoral) and the other side facing outward toward skin. A particular example includes a radiation detector facing outward configured to sense skin response, a temperature sensor facing outward configured to sense skin temperature and a temperature sensor facing inward configured to sense muscle (e.g., core) temperature. As skin is known to respond to temperature differences, measurement of both muscle and skin temperature may aid in determining whether a skin response is due directly or indirectly to temperature, due directly or indirectly to a change in autonomic nerve activity, etc. While various examples mention a pectoral pocket, other locations may be used for implant where a radiation detector can sense skin response (e.g., due to vasoconstriction, vasodilation, etc.).

FIG. 2 shows an exemplary, simplified block diagram depicting various components of the device 100. The device 100 can be capable of treating both fast and slow arrhythmias with stimulation therapy, including cardioversion, defibrillation, and pacing stimulation. As described in more detail below, information acquired from the one or more sensors 272 may aid in diagnosing or confirming a condition and optionally tailoring a therapy to treat a cardiac condition (e.g., adjusting one or more parameters of a therapy). While a particular multi-chamber device is shown, it is to be appreciated and understood that this is for illustration purposes only. Thus, the techniques, methods, etc., described below can be implemented in connection with any suitably configured or configurable device. Accordingly, one of skill in the art could readily duplicate, eliminate, or disable the appropriate circuitry in any desired combination to provide a device capable of treating the appropriate chamber(s) or regions of a patient's heart. Further, various features may be arranged to treat a neural condition such as Parkinson's tremor, Tourette syndrome, pain, depression, etc. (e.g., via deep brain or other nerve stimulation, which may activate or block nerve activity).

Housing 200 for the device 100 is often referred to as the "can", "case" or "case electrode", and may be programmably selected to act as the return electrode for all "unipolar" modes. The housing 200 may be used as a return electrode alone or in combination with one or more of the coil electrodes 126, 132 and 134 for shocking or other purposes. The housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals). As shown in FIG. 1, the housing 200 includes features to accommodate the one or more sensors 272 positioned on a surface configured to be directed toward a patient's skin. The housing 200 may also include features to accommodate one or more sensors 272' on an opposing surface or edge surface (e.g., not directed toward a patient's skin).

To achieve right atrial sensing, pacing and/or other tissue sensing, stimulation, etc., the connector includes at least a right atrial tip terminal ($A_R$ TIP) 202 adapted for connection to the right atrial tip electrode 120. A right atrial ring terminal ($A_R$ RING) 201 is also shown, which is adapted for connection to the right atrial ring electrode 121. To achieve left chamber sensing, pacing, shocking, and/or other tissue sensing, stimulation, etc., the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

To support right chamber sensing, pacing, shocking, and/or other tissue sensing, stimulation, etc., the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses. Where stimulation of tissue other than myocardium is desired, one or more of the generators 222 and 224 may be configured for such stimulation or a device may include one or more other or additional generators (e.g., configured for deep brain stimulation, nerve stimulation, etc.).

The microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

The microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation. In various examples described herein, the detector 234 may be configured to detect an abnormal physiologic condition such as an arrhythmia and issue a signal that causes the device 100 to acquire or to analyze information from the one or more sensors 272 and optionally other information (e.g., activity information, temperature information, etc.). While the detector 234 is configured for detection of an abnormal cardiac condition (e.g., arrhythmia), a device may include, additionally or alternatively, a detector configured for detection of abnormal nerve activity, for example, as associated with a neural disorder (e.g., Parkinson's, Tourette, pain, depression, etc.).

Microcontroller 220 further includes a morphology discrimination module 236, a capture detection module 237 and an auto sensing module 238. The aforementioned components may be implemented in hardware as part of the microcontroller 220, or as software/firmware instructions programmed into the device and executed on the microcontroller 220 during certain modes of operation. The morphology discrimination module 236 may be configured to compare acquired information to one or more criteria, which may be based on previously acquired information. As described herein, such a module may be configured to act on cardiac information, nerve information, muscle information, skin response information, etc. The capture detection module 237, as described herein, may aid in acquisition, analysis, etc., of information relating to IEGMs and, in particular, act to distinguish capture versus non-capture versus fusion. The auto sensing module 238 may function to adjust one or more parameters associated with signal acquisition (e.g., cardiac, nerve, muscle, skin, etc.).

The microcontroller 220 further includes a skin sensing module 239. The module 239 may be used for purposes of acquiring and analyzing skin response information. The module 239 may operate in conjunction with various other modules and/or circuits of the device 100 (e.g., the detector 234, the one or more sensors 272, the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each of the sensing circuits 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with sensing low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation) and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac or other physiologic signals may also be applied to inputs of an analog-to-digital (ND) data acquisition system 252. In the example of FIG. 2, the data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or another lead (e.g., the lead 110) through the switch 226 to sample cardiac signals or other signals across any pair or other number of desired electrodes. A control signal 256 from the microcontroller 220 may instruct the ND 252 to operate in a particular mode (e.g., resolution, amplification, etc.).

Various exemplary mechanisms for signal acquisition optionally include use of one or more analog-to-digital converter. Various exemplary mechanisms may allow for adjustment of one or more parameter associated with signal acquisition (e.g., to improve signal-to-noise, etc.).

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. In the example of FIG. 1, the device 100 is configured to sense and store a relatively large amount of data (e.g., from the data acquisition system 252), which data may then be used for subsequent analysis to guide the programming and operation of the device 100.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, W Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, $O_2$ concentration of blood, pH of blood, $CO_2$ concentration of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiologic sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100 of FIG. 2, which can employ shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

While various features of the device 100 are described with respect to cardiac therapies, as described herein, an exemplary device may include at least some of the features of the device 100 and be configured to deliver a therapy other than a cardiac therapy. For example, an exemplary device may be configured as a deep brain stimulation device or other nerve or muscle stimulation device. With respect to nerve stimulation, autonomic nerves or other types of nerves may be involved with delivery of a particular therapy. Such a device may include sensing of nerve activity (including brain activity) and responding to the sensed activity, for example, by delivering energy to the body (or a chemical substance) in a manner that aims to treat a patient condition. With respect to delivery of a chemical substance, a device may include features of a conventional implantable drug delivery system (e.g., configured to deliver insulin, a pain reliever, a neurostimulant, a neurodepressant, etc.). Such a device typically includes a reservoir and a pumping mechanism to cause material in the reservoir to be delivered in vivo. Such features may be under control of a microprocessor such as the processor 220 of the device 100 of FIG. 2. As described herein, an exemplary implantable device includes one or more sensors to sense skin response. Skin response information may be relied on to diagnose a condition, call for delivery of a therapeutic action, tailor a therapeutic action, etc.

As described herein, resistance to blood flow within a vascular network is typically determined by various factors such as size of individual vessels (e.g., length and diameter), organization of the vascular network (e.g., series and parallel arrangements), physical characteristics of the blood (e.g., viscosity, laminar flow versus turbulent flow), and extravascular mechanical forces acting upon the vasculature. Physical changes in vessel diameter are often the most profound regulators of blood flow, particularly changes in small arteries and arterioles. The skin is a highly perfused organ with many small vessels that respond to various types of internal and external stimuli where stimuli that cause constriction or dilation can drastically alter vascular resistance of skin.

Figure 3:
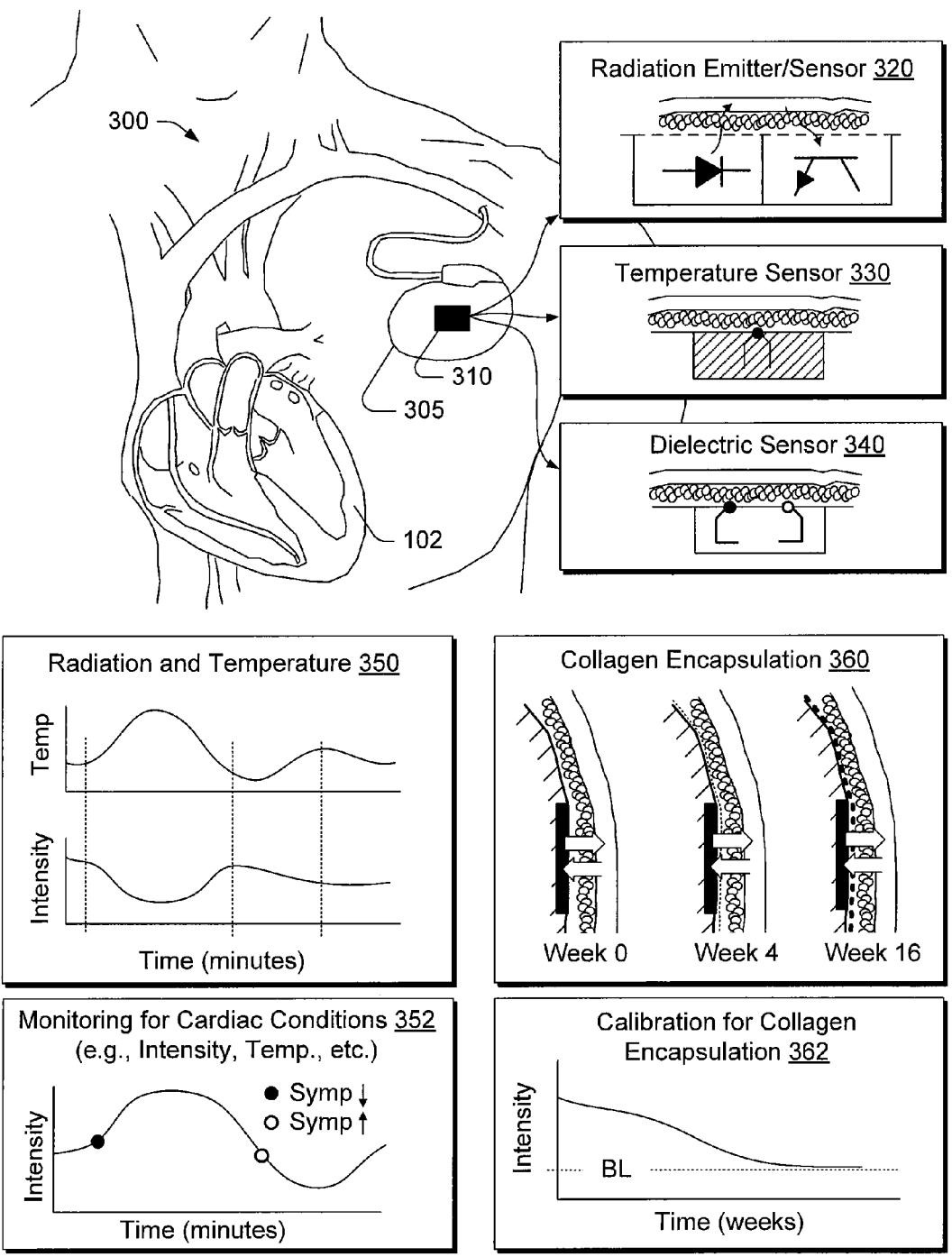
FIG. 3 is a diagram of an exemplary device and one or more sensors and some examples of sensed information and body response to implantation of the device.

FIG. 3 shows an exemplary system 300 where an implantable device 305 includes one or more sensors 310. For example, the one or more sensors 310 may include a radiation sensor 320 configured with a radiation emitter and a radiation sensor, a temperature sensor 330 configured with a thermocouple and a dielectric sensor 340 configured with one or more electrodes. While the sensors 320, 330 and 340 are shown with respect to a surface directed toward a patient's skin, one or more sensors may be oriented away from the patient's skin, for example, on an opposing surface of the device 305. In various examples, a device can include sensors on opposing surfaces (e.g., to measure "core" physiology and to measure "skin" physiology).

The radiation sensor 320 may be a plethysmography sensor configured to sense skin response to vasoconstriction or vasodilation. In such an example, the sensor 320 does not necessarily require features specifically for measuring blood oxygen concentration and may merely include features configured to indicate whether tissue is perfused or not (e.g., due to vasoconstriction or vasodilation). For example, vasoconstriction may make the skin more "white" regardless of the extent to which blood in the skin is oxygenated (e.g., "red") or deoxygenated (e.g., "blue"); correspondingly, vasodilation may make the skin less "white" regardless of the extent to which blood in the skin is oxygenated or deoxygenated;

The sensor 330 may include various features typically associated with temperature measurement circuitry. In the example of FIG. 3, the sensor 330 includes a probe and insulating material to thermally insulate the probe from the can of the device 305. Such an arrangement can make the probe more sensitive to temperature changes in the adjacent skin (e.g., by minimizing conduction from the can to the probe). As described herein, an implantable device may include two or more temperature sensors. For example, the device 305 may include an outward facing temperature sensor to sense skin temperature and an inward facing temperature sensor to sense muscle temperature, which may be representative of core temperature. An exemplary device may optionally rely on a temperature differential between a core and a skin temperature. For example, where a change occurs in the skin temperature due to vasoconstriction, the differential may increase and where a change occurs in the skin temperature due to vasodilation, the differential may decrease. Further, if a patient's core temperature rises before a change in skin temperature, the differential may decrease and indicate that any subsequent change in skin temperature is due to the rise in the core temperature (e.g., increased metabolism due to exercise, etc.).

The sensor 340 may include electrodes configured to measure resistance or conductance. The sensor 340 may include ring-shaped or other shaped electrodes. For example, concentric electrodes (whether circular, oval, polygonal) may be able to cover a larger surface area and be aligned with a direction of contraction or expansion of skin that may accompany vasoconstriction or vasodilation.

A plot 350 of temperature and intensity versus time in minutes shows how intensity may decrease and temperature increase due to vasodilation; how temperature may decrease and intensity increase due to vasoconstriction; and how temperature may increase due to increased metabolism (e.g., shivering) without any change in intensity. A plot 352 of intensity versus time shows various markers that may indicate whether sympathetic activity is increasing or decreasing based on acquired intensity data and optionally other information (e.g., data, model, etc.).

A diagram 360 shows how collagen can encapsulate an implantable device. Such a process may occur over a period of weeks. As described herein, an exemplary method can include acquiring intensity data during an encapsulation period to establish a baseline or otherwise account for collagen encapsulation. A plot 362 of intensity versus time indicates where a baseline value is reached after a period of weeks. In general, a collagen layer tends to be relatively thin, on the order of a millimeter or two. As described herein, a radiation sensor can emit radiation of sufficient intensity to penetrate a collagen layer of a typical thickness such that a radiation detector can detect reflected radiation of at least the dermis of the skin in a manner that can distinguish vasoconstriction or degree of vasoconstriction/vasodilation.

Figure 4:
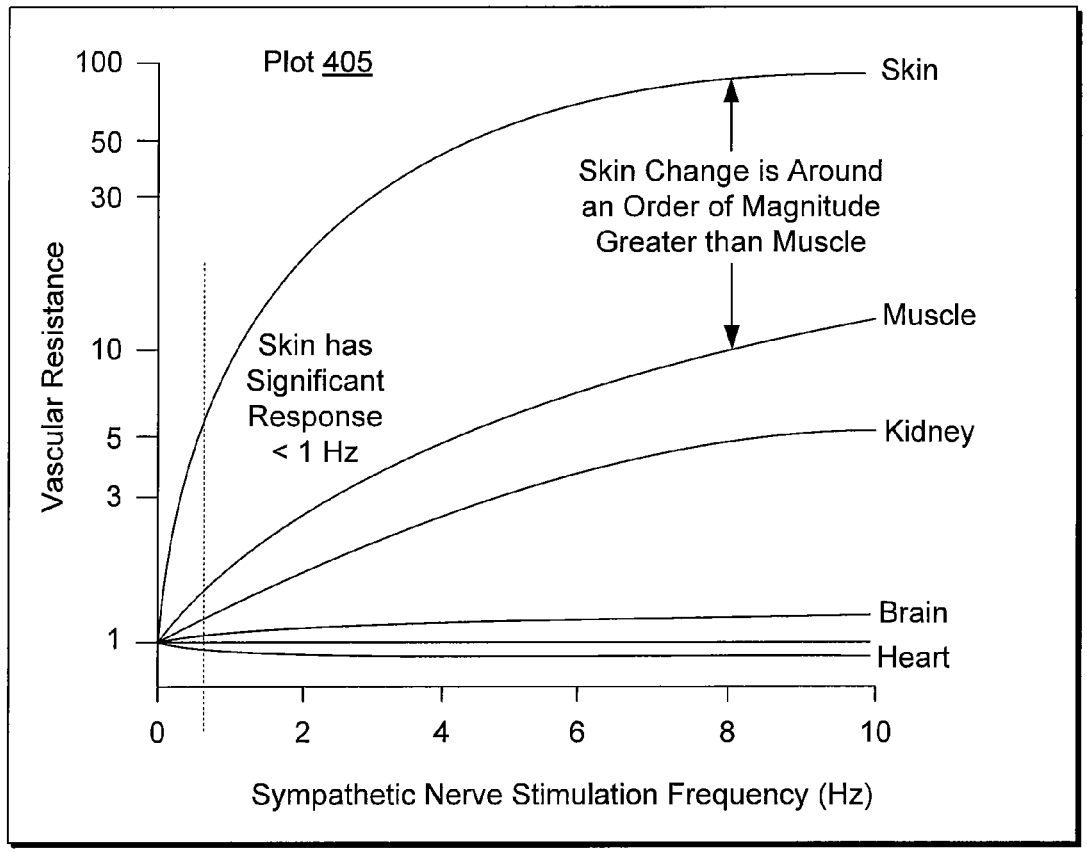
FIG. 4 is a plot of vascular resistance versus sympathetic nerve stimulation frequency and a block diagram of an exemplary method for sensing skin response and adjusting a therapy based at least in part on sensed skin response information.
Figure 4:
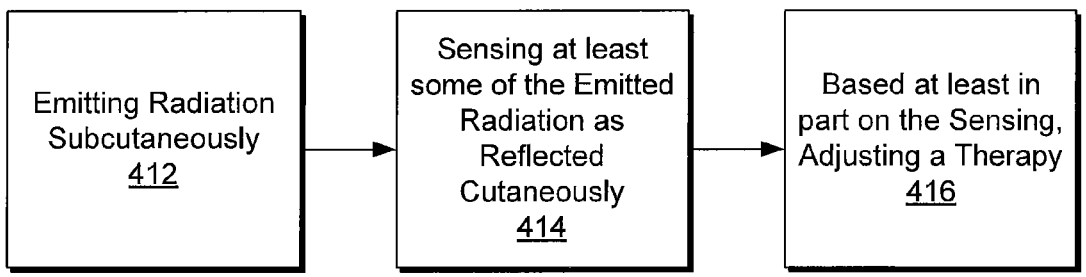

FIG. 4 shows a plot 405 of vascular resistance versus sympathetic nerve stimulation frequency and an exemplary method 410 for adjusting a therapy. The plot 405 shows that vascular resistance of skin changes for frequencies less than 1 Hz and that vascular resistance changes in skin can be over an order of magnitude greater than changes for other organs. As indicated, muscle can exhibit a 10 fold increase in vascular resistance responsive to sympathetic nerve stimulation whereas skin can exhibit about 100 fold increase. Accordingly, a sensor that senses vascular resistance changes in skin can be more sensitive to underlying sympathetic activity than a sensor that senses changes in muscle.

Sympathetic innervation of the skin includes an adrenergic vasoconstrictor system that contributes to resting cutaneous vascular tone and a cholinergic vasodilator system with an unknown neurotransmitter co-released with acetylcholine. While causes of sympathetic activity or lack thereof can be manifold, as described herein, sensing skin provides advantages, especially for situations where an implantable device is conventionally implanted subcutaneously adjacent to a patient's skin (e.g., consider pectoral pocket used for many ICD, brain stimulation devices, etc.).

In the example of FIG. 4, the exemplary method 410 includes emitting radiation subcutaneously 412, sensing at least some of the emitted radiation as reflected cutaneously (i.e., by at least the dermis) and, based at least in part on the sensing, adjusting a therapy 416 (e.g., a cardiac therapy, a neural therapy, etc.).

As described herein, an exemplary method includes emitting radiation subcutaneously; sensing at least some of the emitted radiation as reflected cutaneously; detecting an abnormal physiologic condition such as cardiac arrhythmia; and, based at least in part on the sensing, adjusting a stimulation therapy (e.g., cardiac stimulation) to treat the detected abnormal physiologic condition (e.g., cardiac arrhythmia). Such a method may further include establishing a relationship between cutaneously reflected radiation and one or more types of abnormal physiologic conditions (e.g., cardiac arrhythmia or other conditions). For example, where cutaneously reflected radiation indicates a high degree of vasoconstriction, this may indicate a significant increase in sympathetic activity, which may be associated with a life threatening arrhythmia.

As described herein, various exemplary methods may include sensing temperature subcutaneously, for example, to sense cutaneous temperature. Such a method may include sensing cutaneous temperature (e.g., skin temperature) and sensing muscle temperature (e.g., core temperature). A method may include adjusting a cardiac stimulation therapy to treat a detected cardiac arrhythmia based at least in part on a sensed temperature.

In various examples, skin response sensing may occur prior to detection of cardiac arrhythmia or other condition. In various examples, skin response sensing may occur responsive to detection of cardiac arrhythmia or other condition, which may be an abnormal physiologic condition.

An exemplary method may include implanting a device configured to deliver a cardiac stimulation therapy where the device is also configured to perform, at least, skin response sensing. An exemplary method may include training an implantable device to associate sensed radiation, as reflected cutaneously, with a condition. Such conditions may include one or more of a neurologic condition, a cardiac condition or a neurocardiogenic condition.

As described herein, various exemplary methods may be implemented using one or more computer-readable media that include processor-executable instruction to instruct a device such as the implantable device 100 of FIGS. 1 and 2. For example, one or more computer-readable media may include instructions to instruct a device to emit radiation subcutaneously; sense at least some emitted radiation as reflected cutaneously; detect an abnormal physiologic condition such as cardiac arrhythmia; and, based at least in part on the sensed radiation, to adjust a stimulation therapy to treat a detected abnormal physiologic condition (e.g., to treat cardiac arrhythmia).

As described herein, an exemplary method includes emitting radiation subcutaneously; sensing at least some of the emitted radiation as reflected cutaneously; detecting abnormal neural activity, which may be considered an abnormal physiologic condition; and, based at least in part on the sensing, adjusting a neural stimulation therapy to treat a neural condition associated with the detected abnormal neural activity. Such a method may include establishing a relationship between cutaneously reflected radiation and one or more types of neural conditions. For example, onset of a Parkinson's tremor may cause an increase in sympathetic activity that causes vasoconstriction. Where a sensed skin response indicates that a certain degree of vasoconstriction has occurred, this response may be relied on to determine severity of the tremor and, if sufficiently severe, trigger delivery of deep brain stimulation in an effort to alleviate the tremor.

Various exemplary methods may include sensing temperature subcutaneously, for example, in a manner that senses cutaneous temperature. An exemplary method may include sensing cutaneous temperature (e.g., skin) and sensing muscle temperature (e.g., core). Such temperature sensing may be relied on to adjust a neural stimulation therapy to treat a neural condition.

With respect to skin response sensing and detection of neural activity (e.g., abnormal activity), such sensing may occur prior to detection of neural activity (e.g., where the sensing triggers nerve sensing). A method may include skin response sensing responsive to detection of particular neural activity. For example, where detection of neural activity indicative of pain occurs, an exemplary method may trigger skin response sensing to determine severity of pain based on degree of vasoconstriction as a measure of increased sympathetic activity.

Various exemplary methods may include implanting a device configured to deliver neural stimulation therapy and to perform, at least, skin response sensing. An exemplary method may include training an implantable device to associate sensed radiation, as reflected cutaneously, with a condition where the condition may be a neural condition associated with depression, Parkinson's disease, Tourette syndrome, pain, etc.

As described herein, various exemplary methods may be implemented using one or more computer-readable media that include processor-executable instruction to instruct a device such as the implantable device 100 of FIGS. 1 and 2. For example, one or more computer-readable media may include instructions to instruct a device emit radiation subcutaneously; sense at least some emitted radiation as reflected cutaneously; detect abnormal neural activity; and, based at least in part on the sensed radiation, to adjust a neural stimulation therapy to treat a neural condition associated with detected abnormal neural activity.

As described herein, an exemplary implantable device includes a processor, memory, tissue stimulation circuitry, a radiation emitter, a radiation sensor, one or more temperature sensors, and control logic, implemented at least in part by the processor, where the control logic is configured to assess sensed radiation based at least in part on sensed temperature and to control the tissue stimulation circuitry based at least in part on the assessed radiation. Such a device may include control logic configured to determine whether a change in sensed radiation corresponds to an external change in temperature, to an internal change in temperature, or to a change in autonomic tone.

As mentioned, an exemplary implantable device may include two or more temperature sensors. For example, a device may include a temperature sensor oriented for sensing skin temperature and comprising another temperature sensor oriented for sensing muscle temperature. As mentioned with respect to FIG. 1, an implantable device may have a housing that includes a temperature sensor associated with a surface of the housing and a temperature sensor associated with an opposing surface of the housing (e.g., consider a "puck" shaped housing with sensors on opposing surfaces). In such an example, one temperature sensor may be a skin temperature sensor and the other temperature sensor may be a core temperature sensor. Device circuitry may be optionally configured to provide a signal representative of a temperature differential.

As described herein, an exemplary implantable device may include nerve tissue stimulation circuitry, cardiac tissue stimulation circuitry, brain tissue stimulation circuitry or other type of tissue stimulation circuitry. A device may include multiple types of tissue stimulation circuitry or circuitry configured via control logic to stimulate multiple types of tissue. A device may rely on a multiplexer or other technology to route stimulation energy from a particular stimulation circuit (see, e.g., the example device 100 of FIGS. 1 and 2).

Figure 5:
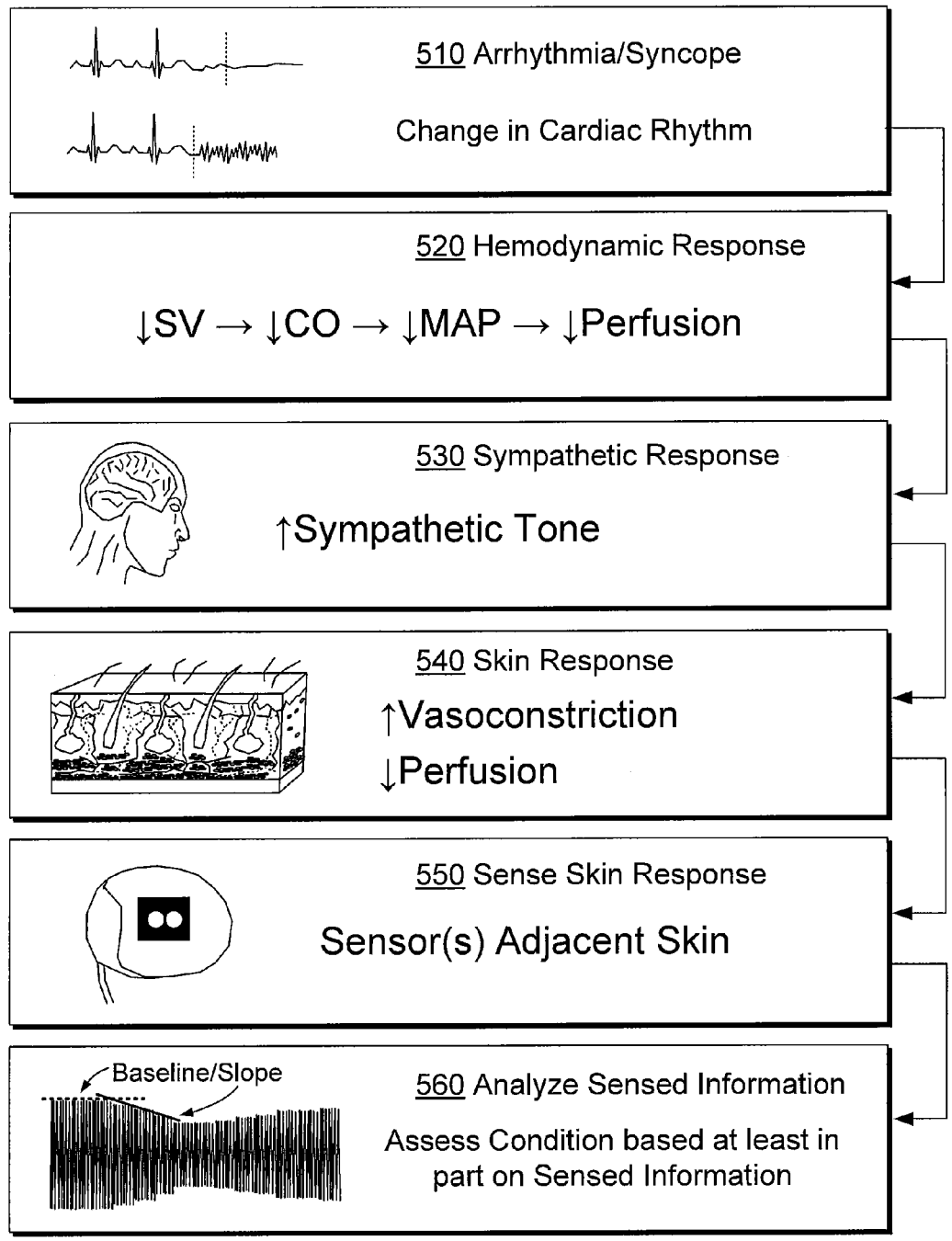
FIG. 5 is a block diagram of an exemplary method that includes sensing skin response as related to cardiac activity.

FIG. 5 shows an exemplary method 500 that includes sensing skin response and assessing sensed skin response. In the example of FIG. 5, the method 500 is response to a change in cardiac rhythm 510 where the change in cardiac rhythm causes a hemodynamic response 520. As indicated, the hemodynamic response 520 may include a chain of events where a decrease in stroke volume (SV) leads to a decrease in cardiac output (CO), which leads to a decrease in mean arterial pressure (MAP) and a corresponding decrease in perfusion. One or more of these changes can cause a sympathetic response 530, such as an increase in sympathetic tone. As mentioned, the skin is highly innervated and hence a skin response 540 may be expected to occur due to the sympathetic response 530. As indicated in FIG. 5, when sympathetic tone increases, vasoconstriction occurs (or increases) and skin perfusion decreases. The method 500 includes sensing skin response 550 using one or more sensors positioned adjacent skin and analyzing sensed information 560, for example, to assess patient condition. In the example of FIG. 5, a signal is shown along with a baseline and a slope. In this example, the slope may indicate that a skin response has occurred, which may be analyzed to determine whether a cardiac event such as arrhythmia or syncope has occurred (e.g., as a proximate cause of the skin response).

As described herein, an arrhythmic/syncopal event can cause varying levels of hemodynamic impairment. In turn, this hemodynamic impairment can cause proportionally varying levels of vasoconstriction in the skin (from low to severe) due to modulation of sympathetic tone. As mentioned, skin response can be measured by a sensor of an implantable device facing upwards towards the skin. As the hypothalamus and medulla oblongata continually integrate sensory information from the entire body in order to maintain homeostasis, these structures are extremely sensitive to changes in hemodynamics. As hemodynamic impairment increases (e.g., due to syncope, arrhythmia, etc.), the medulla proportionally increases sympathetic outflow in order to restore normal hemodynamics and ensure adequate perfusion of critical tissues. The peripheral vascular beds of the skin are extremely sensitive to these changes in sympathetic tone and by extension, to changes in hemodynamics. During episodes of impaired hemodynamics, one of the first visible manifestations is a dramatic reduction in skin perfusion via peripheral vasoconstriction in response to the stimulation of alpha-1 adrenergic receptors.

Further, events such as myocardial infarction can alter vascular resistance and cutaneous circulation. For example, a study by Ratz et al. ("Effects of acute myocardial infarction on the circulation of the conscious rat," J Auton Nery Syst. 1986 August; 16(4):249-59) found that at 48 h post-MI, vascular resistance in the skeletal muscle, spleen, gut and cutaneous circulations were significantly reduced compared to sham-operated rats. Hence, an exemplary method may include establishing a pre-event baseline and comparing skin response information acquired after the event to the pre-event baseline.

As described herein, measuring skin perfusion can be a very sensitive leading indicator of hemodynamic impairment. Further, while a reduction in hemodynamics may never translate into a reduction in blood pressure (unless compensatory mechanisms are exceeded), a reduction is likely to modulate peripheral resistance to some degree via a hard coded autonomic reflex. Detection of such reflexes via skin response information can aid in diagnosing conditions and optionally adjusting a therapy (e.g., to address hemodynamics, neural condition, etc.).

Figure 6:
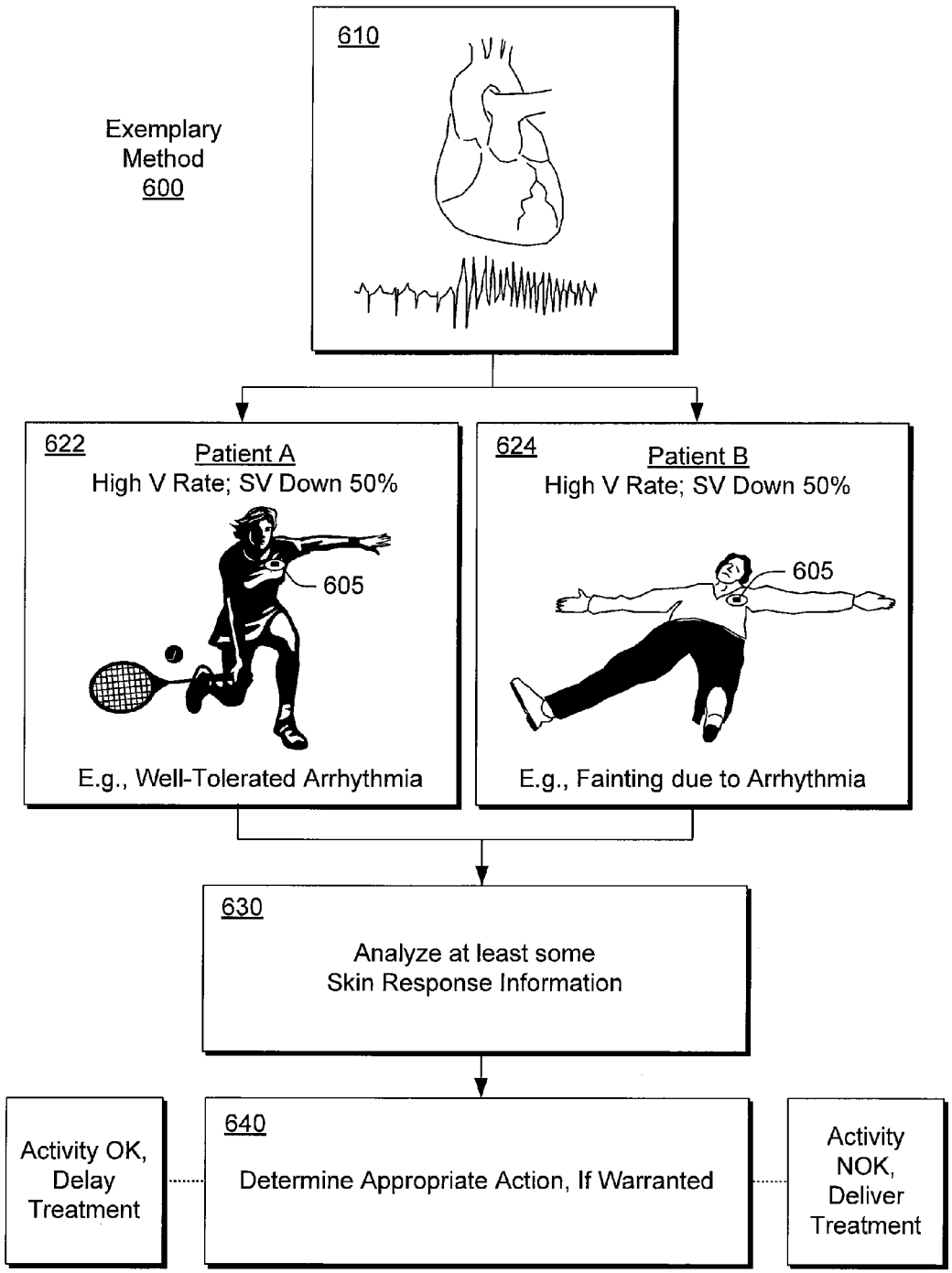
FIG. 6 is a block diagram of an exemplary method that includes sensing skin response and determining appropriate action, if warranted, to treat a condition.

FIG. 6 shows an exemplary method 600 that can determine whether appropriate action should be taken based at least in part on skin response information. In the example of FIG. 6, the method 600 may be responsive to a cardiac event 610, such as an arrhythmia. Patients can respond differently to an arrhythmia, as indicated by Patient A and Patient B. While both patients have a high ventricular rate and reduced stroke volume, Patient A tolerates the arrhythmia and continues activity and Patient B faints due to the effects of the arrhythmia. Where both patients are fitted with an exemplary implantable device 605, the method 600 includes sensing skin response, per block 622 and 624. In an analysis block 630, at least some of the sensed skin response information is analyzed optionally with other information (e.g., temperature, IEGM, accelerometer, etc.). For example, where the device 605 includes circuitry for acquisition of IEGMs, an accelerometer, temperature sensor, etc., such information may be analyzed in conjunction with skin response information. Specifically, where an IEGM indicates that an arrhythmia exists, an exemplary method may analyze skin response information for a time (or period of time) prior to the arrhythmia and a time (or period of time) following onset of the arrhythmia to determine whether a significant hemodynamic change occurred (e.g., as evidenced by vasoconstriction, vasodilation or a combination thereof). In another example, an accelerometer may indicate whether a patient is moving or not moving (e.g., to distinguish whether the arrhythmia is tolerated or not tolerate). Consider Patient A and Patient B where an accelerometer would indicate that Patient A is active while Patient B is inactive (due to fainting).

In the example of FIG. 6, the method 600 includes a determination block 640 that determines appropriate therapeutic action, if warranted. For example, as Patient A tolerates the arrhythmia, action may be unwarranted; whereas, for Patient B, action such as ATP, defibrillation, increased rate, etc., may be warranted.

Tachyarrhythmia therapies traditionally rely on heart rate (R—R intervals) as well as several ancillary algorithms to determine a need for anti-arrhythmic therapy. Often, heart rate alone is insufficient for assessing the severity of an arrhythmia and associated patient risk during the arrhythmia. As described herein, an exemplary method includes determining severity of an arrhythmic event based on skin response as a measure of hemodynamic function. For example, Patient B may be rendered unconscious by a reduction in stroke volume of 25 ml, while Patient A is completely unaware of the arrhythmia. As described herein, an exemplary method can include assessing level of severity of an arrhythmia based at least in part on skin response, in a manner that is patient specific. Such an approach may be used in addition to any other type of "absolute" hemodynamic stability approach.

Figure 7:
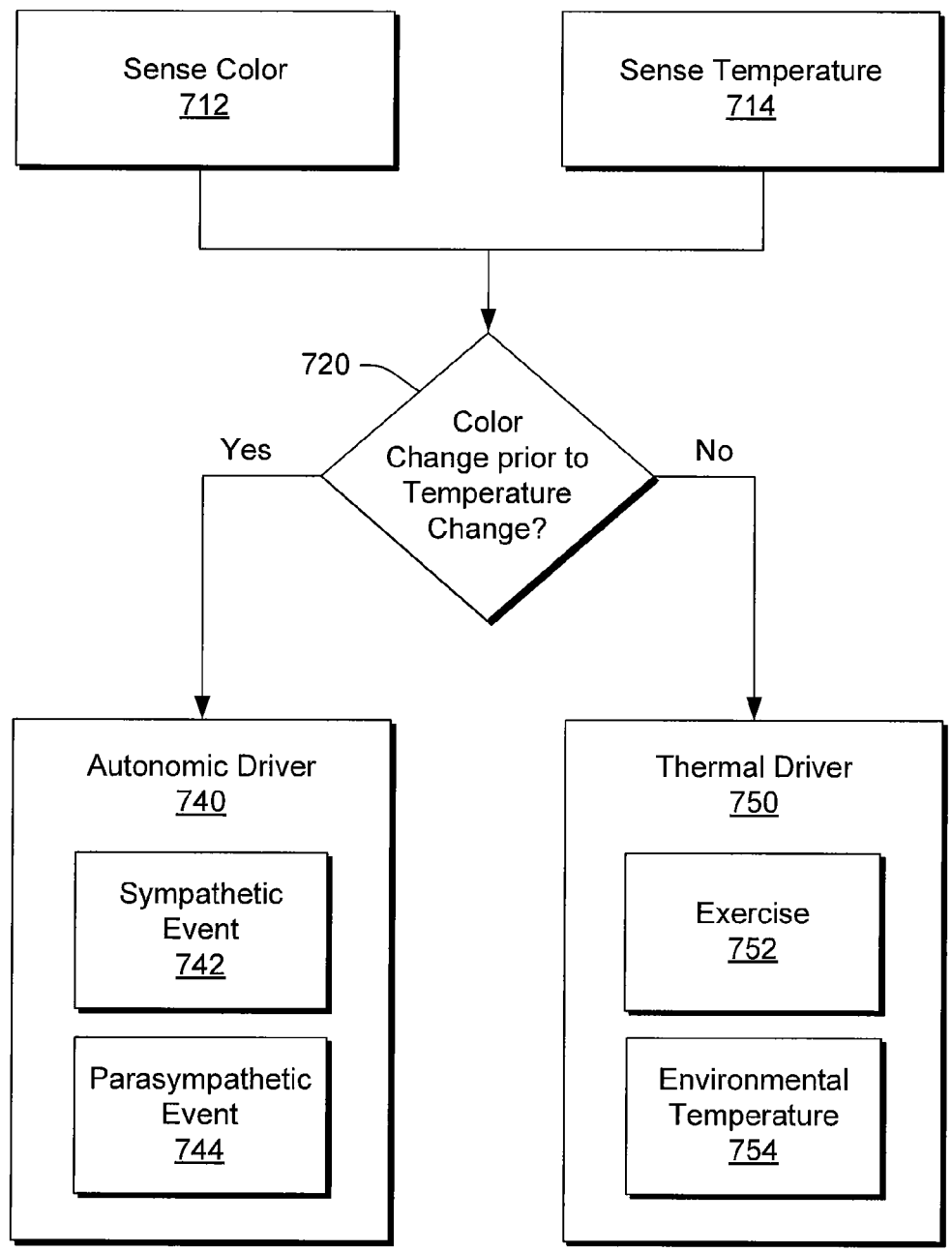
FIG. 7 is a block diagram of an exemplary method that includes sensing skin color and sensing temperature to, for example, determine whether an autonomic driver or a thermal driver is associated with sensed skin response.

FIG. 7 shows an exemplary method 700 that includes sensing skin response 712 and sensing temperature 714. In the example of FIG. 7, the skin response is sensed, for example, as a color change, which may be unrelated to the level of oxygenation or deoxygenation of blood. Specifically, according to the method 700, the skin changes color responsive to vasoconstriction and vasodilation. An exemplary implantable device may include a radiation detector configured to analyze wavelength and optionally intensity of detected light to determine whether a shift is occurring that would indicate a state or a change in blood flow in skin (e.g., homeostatic, vasoconstriction or vasodilation). Depending on the location of the detector, light external to the body could be relied on as a source of radiation or a subcutaneous emitter could be relied on as a source of radiation.

Referring again to the method 700 of FIG. 7, a decision block 720 decides whether a color change of the skin occurred prior to a temperature change. If the decision block 720 decides that a color changed occurred prior to a temperature change, then the method 700 proceeds to an autonomic driver block 740; otherwise, the method 700 proceeds to a thermal driver block 750.

The autonomic driver block 740 pertains to situations where a color change due to a sympathetic event 742 or a parasympathetic event 744 occurs that may then cause a change in skin temperature. The thermal driver block 750 pertains to situations where an internal condition or state such as exercise 752 or an external condition or state such as environmental temperature 754 changes and, in turn, causes a change in skin color.

The method 700 can be used to distinguish temperature induced changes in skin color from autonomic induced changes in skin color. In either instance, the method 700 may further include adjusting a therapy based at least in part on whether sensed information indicates an autonomic driver 740 or a thermal driver 750.

Figure 8:
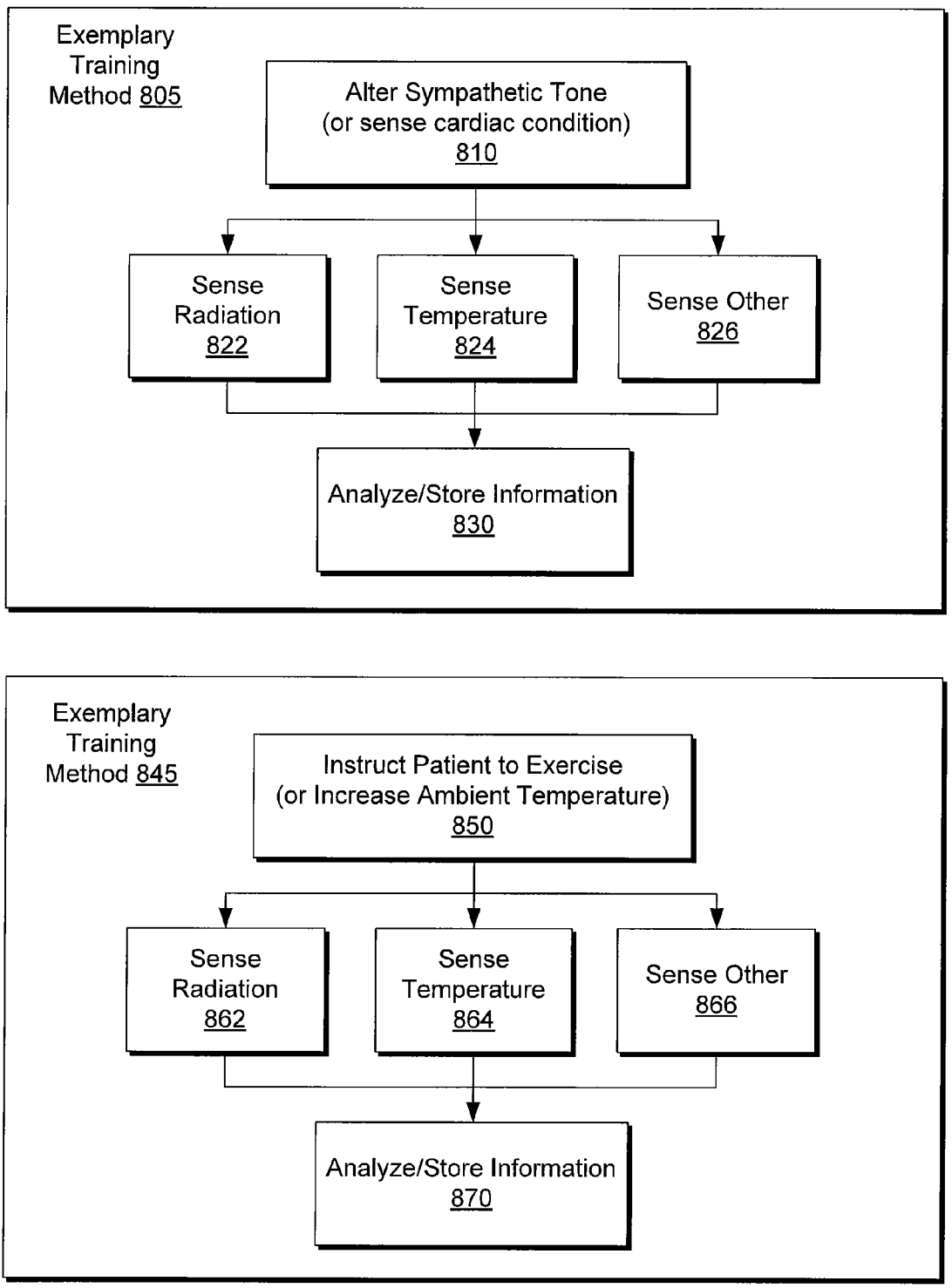
FIG. 8 is a block diagram of exemplary methods for training based on information acquired from one or more sensors.

FIG. 8 shows two exemplary methods 805 and 845 for training an exemplary device or model. The method 805 includes an alteration block 810 that includes altering sympathetic tone of a patient. With respect to the alteration block 810, a patient may experience a natural condition or be subject to an artificial condition (e.g., a drug, cardiac stimulation, nerve stimulation, visual stimulation, aural stimulation, a physical stimulation, etc.) that alters sympathetic tone. One or more sense blocks 822, 824 and 826 sense information that may change in response to the altering of the patient's sympathetic tone. In the example of FIG. 8, the sense block 822 senses radiation (e.g., visible, UV, IR, etc.), the sense block 824 senses temperature and the sense block 826 senses one or more other measures. An analysis and storage block 830 analyzes the sensed information and associates it with the alteration of the patient's sympathetic tone. The block 830 may store the analyzed information in the form of a model, a look-up table, a filter, etc. Accordingly, when one or more sensors sense information, including skin response information, the sensed information may be compared to or analyzed using stored information.

The method 845 includes an instruction block 850 that may instruct a patient to exercise or instruct a temperature controller to change an environmental temperature. The instruction block 850 intends to generate a condition or conditions that may cause a skin response. For example, an increase in environmental temperature may cause a decrease in vascular resistance that allows for skin perfusion and sweating or a decrease in environmental temperature may cause an increase in vascular resistance that acts to reduce blood flow to the skin. Where an instruction instructs a patient to exercise, this may cause a rise in body temperature (i.e., from the inside out), which, in turn, causes a skin response. One or more sense blocks 862, 864 and 866 sense information that may change in response to the instructing, whether directly or indirectly. In the example of FIG. 8, the sense block 862 senses radiation (e.g., visible, UV, IR, etc.), the sense block 864 senses temperature and the sense block 866 senses one or more other measures. An analysis and storage block 870 analyzes the sensed information and associates it with the instruction or an associated condition (e.g., rise in internal body temperature, rise in environmental temperature, decrease in environmental temperature, etc.). The block 870 may store the analyzed information in the form of a model, a look-up table, a filter, etc. Accordingly, when one or more sensors sense information, including skin response information, the sensed information may be compared to or analyzed using stored information.

An exemplary method may include both the training method 805 and the training method 845. As described herein, such an approach can help determine a driver for a skin response (e.g., autonomic driver or other driver).

Figure 9:
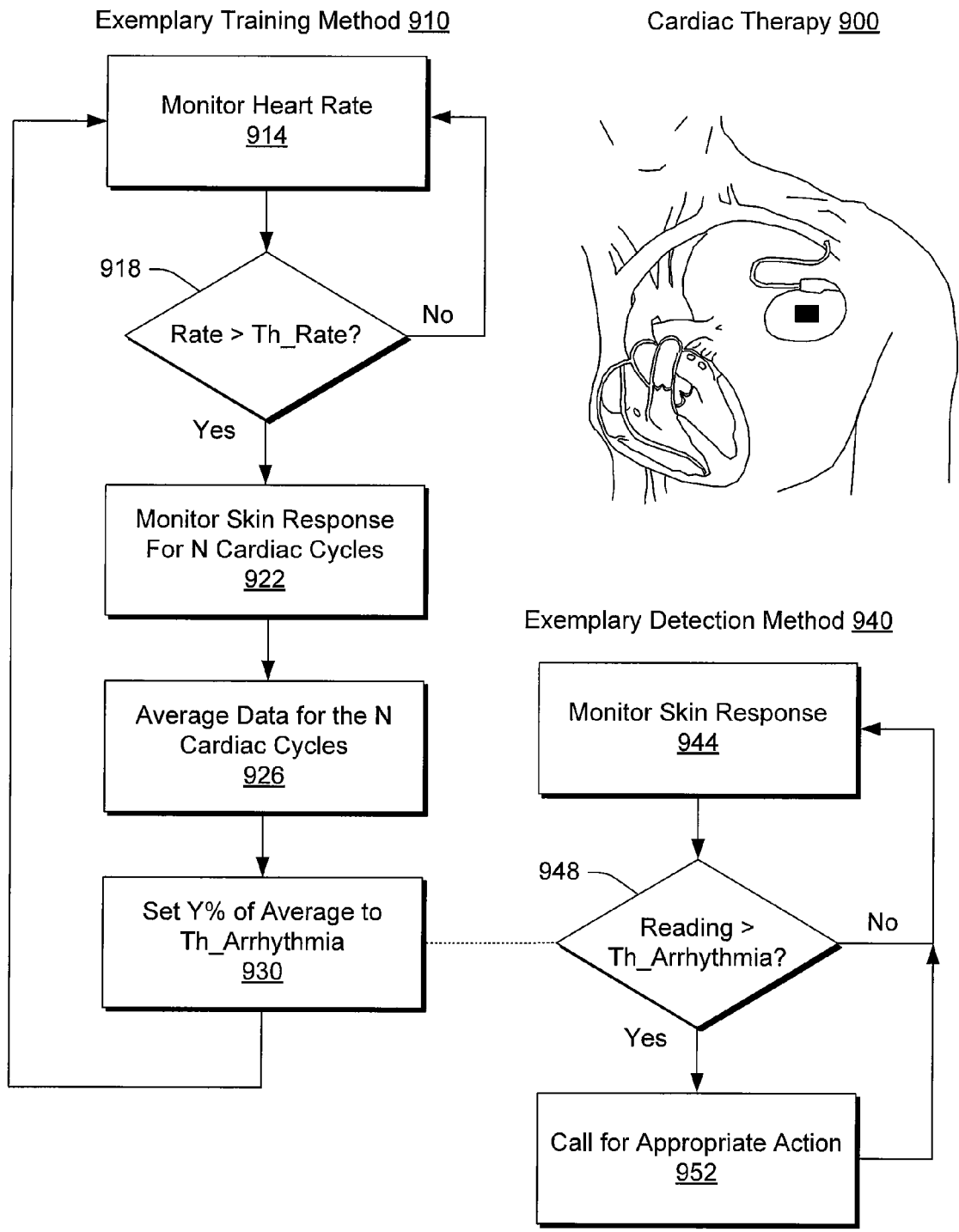
FIG. 9 is a block diagram of an exemplary method for training and an exemplary method for detection with respect to a cardiac therapy.

FIG. 9 shows an exemplary training method 910 and an exemplary detection method 940 as associated with a cardiac therapy 900. The method 910 includes a monitor block 914 that monitors heart rate. A decision block 918 decides whether the heart rate is greater than a threshold heart rate. If the decision block 918 decides that the heart rate is not greater than the threshold heart rate, the method 910 continues at the monitor block 914. However, if the decision block 918 decides that the heart rate is greater than the threshold heart rate, the method 910 continues at a monitor block 922 that monitors skin response. As shown in the example of FIG. 9, the monitor block 922 may monitor skin response for a number of cardiac cycles, based on detection of cycles or a period of time (e.g., if a cycle is not detectable). In an average block 926, the method 910 averages the data for the number of cardiac cycles to generate an average value for a skin response associated with the elevated heart rate. Next, a set block 930 sets a threshold for triggering a therapy where the threshold is based at least in part on the average. In the example of FIG. 9, the threshold is based on a percentage "Y", which may be equal to, greater than or less than 100% (e.g., depending on the nature of the skin response monitoring and optionally for tuning). The method 910 may occur continuously and act to update the threshold for triggering a therapy based on the most recent occurrence of an elevated heart rate.

The method 940 includes a monitor block 944 for monitoring skin response. In the example of FIG. 9, a decision block 948 relies on the threshold for triggering a therapy as determined by the training method 910. Per the decision block 948, if a skin response reading exceeds the threshold, the method 940 continues at a call block 952 that calls for appropriate action; otherwise, the method 940 continues at the monitor block 944. With respect to an appropriate action, where the threshold corresponds to an elevated heart rate (e.g., an arrhythmia), the appropriate action may be a cardiac stimulation therapy for treating the elevated heart rate and returning the heart rate to a normal rate or below a pacing rate.

Figure 10:
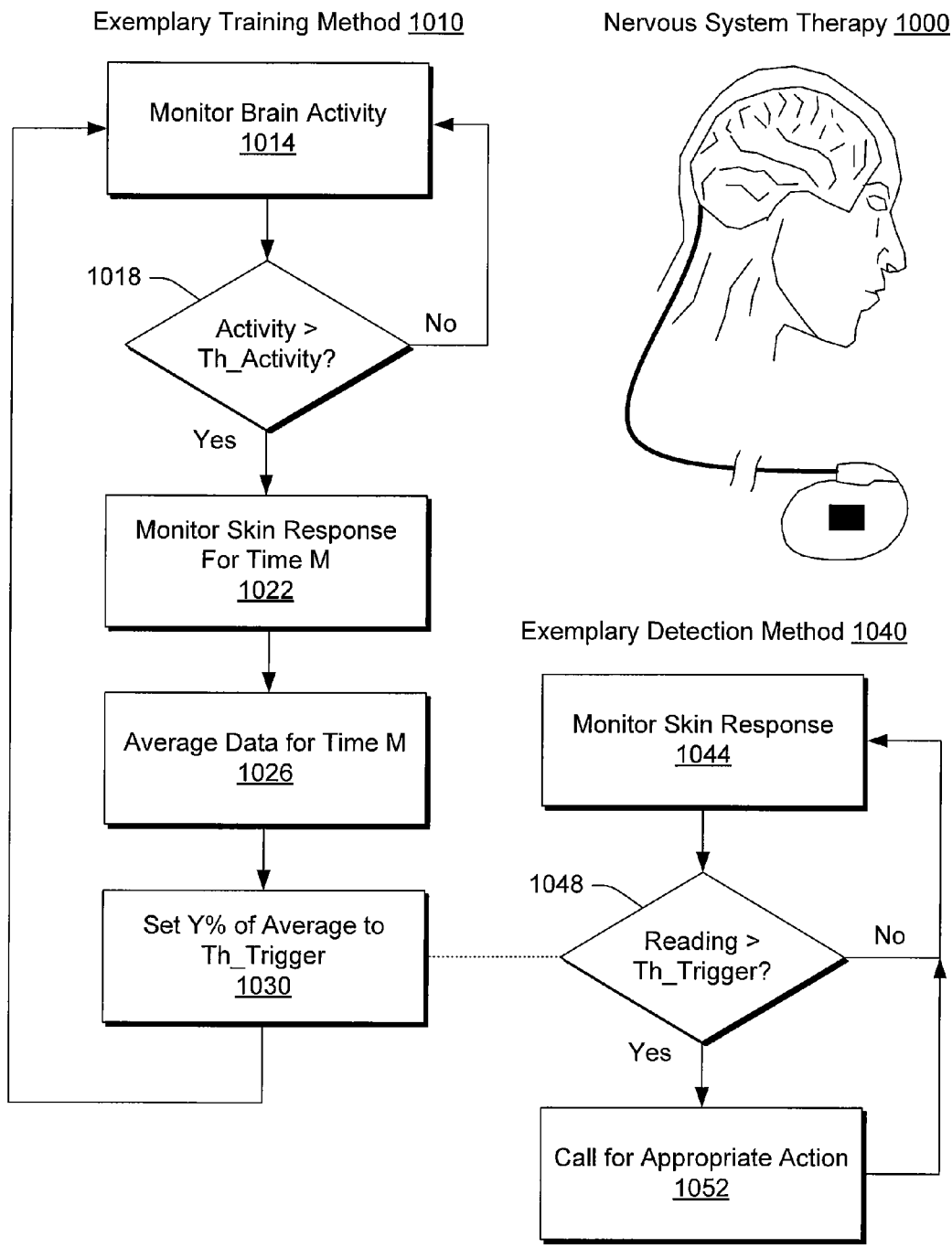
FIG. 10 is a block diagram of an exemplary method for training and an exemplary method for detection with respect to a nervous system therapy.

FIG. 10 shows an exemplary training method 1010 and an exemplary detection method 1040 as associated with a nervous system therapy 1000. The method 1010 includes a monitor block 1014 that monitors brain activity. For example, activity of the subthalamic nucleus (SNT) may be monitored to assess pain, Parkinson's tremor, Tourette syndrome, depression, etc. A decision block 1018 decides whether the activity is greater than an activity threshold (e.g., amplitude, frequency, etc.). If the decision block 1018 decides that the brain activity is not greater than the activity threshold, the method 1010 continues at the monitor block 1014. However, if the decision block 1018 decides that the brain activity is greater than the activity threshold, the method 1010 continues at a monitor block 1022 that monitors skin response. As shown in the example of FIG. 10, the monitor block 1022 may monitor skin response for a period of time "M". Alternatively, skin response may be monitored for a number of brain wave cycles, based on detection of cycles or a period of time (e.g., if a cycle is not detectable). In an average block 1026, the method 1010 averages the data for the period of time M to generate an average value for a skin response associated with the brain activity. Next, a set block 1030 sets a threshold for triggering a therapy where the threshold is based at least in part on the average. In the example of FIG. 10, the threshold is based on a percentage "Y", which may be equal to, greater than or less than 100% (e.g., depending on the nature of the skin response monitoring and optionally for tuning). The method 1010 may occur continuously and act to update the threshold for triggering a therapy based on the most recent occurrence of brain activity exceeding the threshold.

The method 1040 includes a monitor block 1044 for monitoring skin response. In the example of FIG. 10, a decision block 1048 relies on the threshold for triggering a therapy as determined by the training method 1010. Per the decision block 1048, if a skin response reading exceeds the threshold, the method 1040 continues at a call block 1052 that calls for appropriate action; otherwise, the method 1040 continues at the monitor block 1044. With respect to an appropriate action, where the threshold corresponds to abnormal brain activity (e.g., Parkinson's tremor, pain, etc.), the appropriate action may be a nerve or deep brain stimulation therapy for treating the abnormal brain activity or a consequence thereof (e.g., pain) and optionally returning brain activity to normal.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   sensing one or more physiological parameters;
   emitting radiation subcutaneously;
   sensing at least some of the emitted radiation as reflected cutaneously;
   detecting an abnormal physiologic condition based at least in part on the sensed one or more physiological parameters; and
   based at least in part on the sensing of at least some of the emitted radiation, adjusting a stimulation therapy to treat the detected abnormal physiologic condition.

2. The method of claim 1 wherein the detecting an abnormal physiologic condition comprises detecting a cardiac arrhythmia and wherein the adjusting a stimulation therapy comprises adjusting a cardiac stimulation therapy to treat the detected cardiac arrhythmia.

3. The method of claim 2 further comprising establishing a relationship between cutaneously reflected radiation and one or more types of cardiac arrhythmia.

4. The method of claim 2 further comprising sensing temperature.

5. The method of claim 4 wherein the sensing temperature comprises sensing cutaneous temperature and sensing muscle temperature.

6. The method of claim 4 wherein the adjusting a cardiac stimulation therapy to treat the detected cardiac arrhythmia comprises adjusting based at least in part on the sensing temperature.

7. The method of claim 1 further comprising training an implantable device to associate sensed radiation, as reflected cutaneously, with a condition.

8. The method of claim 7 wherein the condition comprises a condition selected from a group consisting of neurologic conditions, cardiac conditions and neurocardiogenic conditions.

9. The method of claim 1 wherein the sensing one or more physiological parameters comprises sensing one or more neural activity signals and wherein the detecting an abnormal physiologic condition comprises detecting abnormal neural activity and wherein the adjusting a stimulation therapy comprises adjusting a neural stimulation therapy to treat a neural condition associated with the detected abnormal neural activity.

10. The method of claim 9 further comprising establishing a relationship between cutaneously reflected radiation and one or more types of neural conditions.

11. The method of claim 9 further comprising sensing temperature.

12. The method of claim 11 wherein the sensing temperature comprises sensing cutaneous temperature and sensing muscle temperature.

13. The method of claim 11 wherein the adjusting a neural stimulation therapy to treat the neural condition comprises adjusting based at least in part on the sensing temperature.

14. The method of claim 9 further comprising training an implantable device to associate sensed radiation, as reflected cutaneously, with an abnormal neural condition.

15. The method of claim 14 wherein the condition comprises a condition selected from a group consisting of depression, Parkinson's disease, Tourette syndrome and pain.

16. One or more computer-readable media comprising processor-executable instruction to instruct a device to:
   sense one or more physiological parameters;
   emit radiation subcutaneously;
   sense at least some emitted radiation as reflected cutaneously;
   detect an abnormal physiologic condition based at least in part on the sensed one or more physiological parameters; and
   based at least in part on the sensing of at least some of the emitted radiation, adjusting a stimulation therapy to treat the detected abnormal physiologic condition.

17. An implantable medical device comprising:
   means for sensing one or more physiological parameters;
   means for emitting radiation subcutaneously;
   means for sensing at least some of the emitted radiation as reflected cutaneously;
   means for detecting an abnormal physiologic condition based at least in part on the sensed one or more physiological parameters; and
   based at least in part on the sensing of at least some of the emitted radiation, means for adjusting a stimulation therapy to treat the detected abnormal physiologic condition.

18. The implantable medical device of claim 17 wherein the means for detecting an abnormal physiologic condition comprises means for detecting a cardiac arrhythmia and wherein the means for adjusting a stimulation therapy comprises means for adjusting a cardiac stimulation therapy to treat the detected cardiac arrhythmia.

19. The implantable medical device of claim 17 wherein the means for detecting an abnormal physiologic condition comprises means for detecting abnormal neural activity and wherein the means for adjusting a stimulation therapy comprises means for adjusting a neural stimulation therapy to treat a neural condition associated with the detected abnormal neural activity.

20. The implantable medical device of claim 17 further comprising means for sensing temperature and means for further adjusting the stimulation therapy to treat the detected abnormal physiologic condition as a function of the sensed temperature.

21. An implantable device comprising:
   a processor;
   memory;
   tissue stimulation circuitry;
   a radiation emitter;
   a radiation sensor;
   one or more temperature sensors; and
   control logic implemented at least in part by the processor, the control logic configured to assess sensed radiation based at least in part on sensed temperature and to control the tissue stimulation circuitry based at least in part on the assessed radiation.

* * * * *